(12) United States Patent
Lasarov et al.

(10) Patent No.: US 11,243,165 B2
(45) Date of Patent: Feb. 8, 2022

(54) SENSOR ARRANGEMENT FOR A PHYSIOLOGICAL MEASUREMENT SENSOR

(71) Applicant: Nokia Technologies Oy, Espoo (FI)

(72) Inventors: Harri Lasarov, Espoo (FI); Joni Jantunen, Helsinki (FI); Leo Karkkainen, Helsinki (FI); Tuomo Latva-Kayra, Espoo (FI)

(73) Assignee: Nokia Technologies Oy, Espoo (FI)

( * ) Notice: Subject to any disclaimer, the term of this patent is extended or adjusted under 35 U.S.C. 154(b) by 236 days.

(21) Appl. No.: 16/463,461

(22) PCT Filed: Dec. 4, 2017

(86) PCT No.: PCT/FI2017/050854
§ 371 (c)(1),
(2) Date: May 23, 2019

(87) PCT Pub. No.: WO2018/122447
PCT Pub. Date: Jul. 5, 2018

(65) Prior Publication Data
US 2019/0360928 A1  Nov. 28, 2019

(30) Foreign Application Priority Data

Dec. 29, 2016 (EP) .................................. 16207218

(51) Int. Cl.
*G01N 21/47* (2006.01)
*A61B 5/024* (2006.01)
*A61B 5/1455* (2006.01)

(52) U.S. Cl.
CPC ....... *G01N 21/474* (2013.01); *A61B 5/02427* (2013.01); *A61B 5/02438* (2013.01);
(Continued)

(58) Field of Classification Search
CPC .............. G01N 21/474; A61B 5/02427; A61B 5/02438; A61B 5/14552;
(Continued)

(56) References Cited

U.S. PATENT DOCUMENTS 5,891,022 A * 4/1999 Pologe ................. A61B 5/6826
600/323
9,241,644 B2 1/2016 Yamashita et al. ........... 356/445
(Continued)

FOREIGN PATENT DOCUMENTS

CN 105380634 A 3/2016
CN 106132299 A 11/2016
(Continued)

*Primary Examiner* — Eric F Winakur
*Assistant Examiner* — Abid A Mustansir
(74) *Attorney, Agent, or Firm* — Harrington & Smith (57) ABSTRACT

An apparatus including a plurality of light sources configured to emit light for reflection from tissue of a user wearing the apparatus, at least one light detector configured to detect light that enters the light detector to produce a detected signal for a physiological measurement, and a light-conducting element configured to conduct light to the light detector, wherein the apparatus is configured to allow light reflected from the tissue of the user to enter the light-conducting element at a plurality of spatially separated locations.

18 Claims, 6 Drawing Sheets

(52) U.S. Cl.
CPC .. *A61B 5/14552* (2013.01); *A61B 2562/0233* (2013.01); *A61B 2562/146* (2013.01)

(58) Field of Classification Search
CPC ...... A61B 2562/0233; A61B 2562/146; A61B 2562/0238; A61B 2562/185; A61B 5/681; A61B 5/0295; A61B 5/6802; A61B 2560/0462; A61B 2562/04; A61B 2562/164; A61B 5/02416
See application file for complete search history.

(56) References Cited

U.S. PATENT DOCUMENTS

| | | | |
|---|---|---|---|
| 2004/0236227 A1* | 11/2004 | Gueissaz | A61B 5/681 600/473 |
| 2011/0118574 A1 | 5/2011 | Chang et al. | 600/324 |
| 2013/0261415 A1 | 10/2013 | Ashe et al. | 600/324 |
| 2014/0107495 A1 | 4/2014 | Marinelli et al. | 600/476 |
| 2016/0278645 A1 | 9/2016 | Yoon | |
| 2016/0367187 A1 | 12/2016 | Ahmed et al. | 5/681 |
| 2017/0181636 A1* | 6/2017 | Luo | A61B 5/6847 |
| 2018/0132766 A1* | 5/2018 | Lee | A61B 5/4872 |
| 2018/0333053 A1* | 11/2018 | Verkruijsse | A61B 5/0077 |
| 2019/0360928 A1 | 11/2019 | Lasarov et al. | 21/474 |

FOREIGN PATENT DOCUMENTS

| | | |
|---|---|---|
| JP | 2013-176518 | 9/2013 |
| TW | 201117775 A | 6/2011 |

\* cited by examiner

SENSOR ARRANGEMENT FOR A PHYSIOLOGICAL MEASUREMENT SENSOR

CROSS REFERENCE TO RELATED APPLICATION

This patent application is a U.S. National Stage application of International Patent Application Number PCT/FI2017/050854 filed Dec. 4, 2017, which is hereby incorporated by reference in its entirety, and claims priority to EP 16207218.5 filed Dec. 29, 2016.

TECHNICAL FIELD

The present application generally relates to sensor arrangements for physiological measurement sensors.

BACKGROUND

This section illustrates useful background information without admission of any technique described herein representative of the state of the art.

Various metering devices that measure physiological conditions of users such as pulse sensors have become common for people to measure their own heart rate, movements or other physiological parameters or bio signals. The measurements can be performed for example using a chest strap that is worn under clothes or using a wrist worn watch-like sensor device. The sensors measure physiological conditions of a user and produce sensor signals corresponding to a property of the skin of the user or underlying matter (capillaries and veins, for example).

Pulse or heart rate can be monitored for example optically using a photoplethysmography (PPG) sensor. One challenge with PPG measurement is that the measurement is sensitive for sensor location. One should perform the measurement at optimum capillary beds or artery veins to obtain good quality and reliable PPG signals.

SUMMARY

Various aspects of examples of the invention are set out in the claims.

According to a first example aspect of the present invention, there is provided an apparatus comprising:
  a plurality of light sources configured to emit light for reflection from tissue of a user wearing the apparatus,
  at least one light detector configured to detect light that enters the light detector to produce a detected signal for a physiological measurement, and
  a light-conducting element configured to conduct light to the light detector, wherein the apparatus is configured to allow light reflected from the tissue of the user to enter the light-conducting element at a plurality of spatially separated locations.

In an embodiment, the apparatus comprises openings at said plurality of locations, the openings allowing light to enter the light-conducting element. That is, there is an opening at each of said locations.

In an embodiment, said plurality of light sources are arranged into a plurality of sensing regions, each sensing region comprising at least one light source, and wherein the light-conducting element extends through the sensing regions, each sensing region comprising at least one of said openings in vicinity of the respective light source.

In an embodiment, the light-conducting element is a longitudinal element, with one end of the light conducting-element being coupled to the light detector and the other end longitudinally extending away from the light detector, and wherein plurality of said light sources and said openings are located along the length of the light-conducting element.

In an embodiment, the light-conducting element is a light guide.

In an embodiment, the apparatus comprises a diffractive structure at said plurality of locations to guide the light reflected from the tissue of the user into the light-conducting element.

In an embodiment, the diffractive structure comprises one or more of the following: a diffractive optical element, a diffraction grating, a periodic diffractive pattern, and a series of diffraction lines.

In an embodiment, the apparatus comprises a plurality of or more than one of said light detectors.

In an embodiment, the apparatus comprises a plurality of or more than one of said light-conducting elements.

In an embodiment, the apparatus comprises two or more pairs of said light detectors and light-conducting elements.

An embodiment provides a user wearable apparatus comprising the apparatus of the first aspect.

According to a second example aspect of the present invention, there is provided a method for using a sensor arrangement of a user wearable apparatus; the sensor arrangement comprising
  a plurality of light sources configured to emit light for reflection from tissue of a user wearing the user wearable apparatus,
  at least one light detector configured to detect light that enters the light detector to produce a detected signal for a physiological measurement, and
  a light-conducting element configured to conduct light to the light detector, wherein the sensor arrangement is configured to allow light reflected from the tissue of the user to enter the light-conducting element at a plurality of spatially separated locations, wherein the method comprises
  obtaining a plurality of measurement signals using different light sources, and based on the obtained measurement signals, selecting one or more light sources for use in the physiological measurement.

In an embodiment, the method further comprises selectively turning on and off the plurality of light sources to obtain the plurality of measurement signals.

In an embodiment, the method further comprises selectively opening and closing the spatially separate locations to obtain the plurality of measurement signals.

In an embodiment, the method further comprises selecting those one or more light sources that provide a signal that meets a pre-defined quality criterion.

According to a third example aspect of the present invention, there is provided a computer program comprising computer executable program code configured to control a wearable device, when the computer executable program code is executed, to perform the method of the second aspect.

The computer program may be stored in a computer readable memory medium. The memory medium may be a non-transitory memory medium.

Any foregoing memory medium may comprise a digital data storage such as a data disc or diskette, optical storage, magnetic storage, holographic storage, opto-magnetic storage, phase-change memory, resistive random access memory, magnetic random access memory, solid-electrolyte memory, ferroelectric random access memory, organic memory or polymer memory. The memory medium may be formed into a device without other substantial functions than storing memory or it may be formed as part of a device with other functions, including but not limited to a memory of a computer, a chip set, and a sub assembly of an electronic device.

Different non-binding example aspects and embodiments of the present invention have been illustrated in the foregoing. The embodiments in the foregoing are used merely to explain selected aspects or steps that may be utilized in implementations of the present invention. Some embodiments may be presented only with reference to certain example aspects of the invention. It should be appreciated that corresponding embodiments may apply to other example aspects as well.

BRIEF DESCRIPTION OF THE DRAWINGS

For a more complete understanding of example embodiments of the present invention, reference is now made to the following descriptions taken in connection with the accompanying drawings in which.

DETAILED DESCRIPTION OF THE DRAWINGS

Example embodiments of the present invention and its potential advantages are understood by referring to FIGS. 1 through 8 of the drawings. In this document, like reference signs denote like parts or steps.

In various example embodiments of the invention there is provided a new type of a sensor arrangement particularly suited for user wearable optical sensor devices.

In the following, various example embodiments are discussed in connection with optical heart rate sensors such as photoplethysmography (PPG) sensors. Various embodiments are however not necessarily limited to these sensor types only. Instead the sensor arrangement of example embodiments can be used in monitoring of some other physiological condition, too. Physiological conditions referred to herein may include one or more of the following: heart rate, blood pressure, skin moisture, sweating, skin conductance, skin resistance, skin impedance, impedance cardiogram, oxygen saturation level, blood glucose level. In general the sensor arrangement of various embodiments is usable for monitoring physiological conditions of a user from property of the skin of the user or matter underlying the skin of the user (capillaries and veins, for example).

Figure 1:
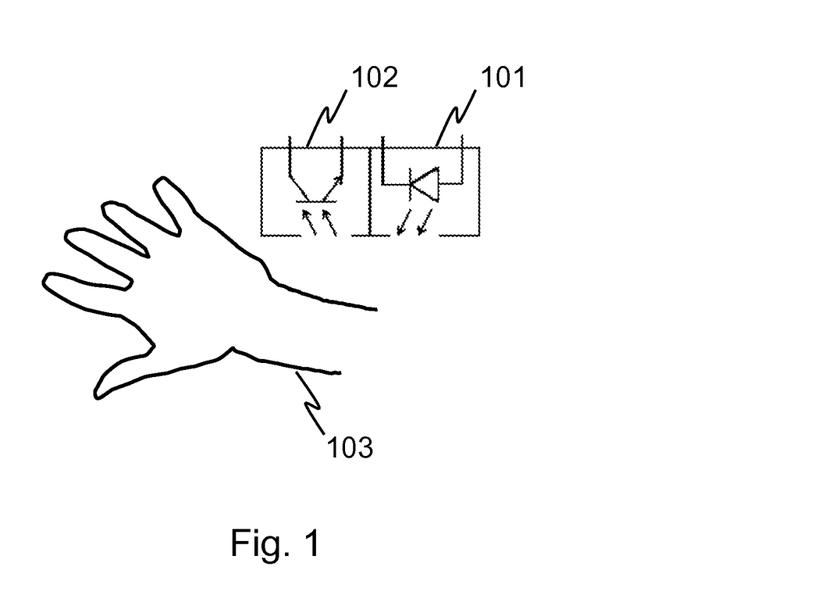
FIG. 1 is a simplified illustration of an example optical heart rate measurement.

FIG. 1 is a simplified illustration of an example optical heart rate measurement. FIG. 1 shows a simple reflective type PPG sensor that comprises a LED (light emitting diode) 101, a light source, and a photo diode (PD) 102, a light detector. The LED (optical emitter, light source) 101 emits light and the light detector 102 receives light rays reflected e.g. from a wrist 103 of a user.

In various embodiments there is provided a new sensor arrangement for physiological measurements. There is a longitudinal light-conducting element configured to guide light to the light detector from multiple locations along the length of the light-conducting element. The light is allowed to enter the light-conducting element from the sides of the light-conducting element along the length of the light-conducting element (i.e. in the middle of the light-conducting element) and not only from the ends of the light-conducting element. There are multiple light sources in vicinity of these locations to enable measurement at different locations. In different implementation examples there may exist one light-conducting element and one light detector, or one light-conducting element and more than one light detectors, or more than one light-conducting elements and one light detector, or more than one light-conducting elements and more than one light detectors. More detailed implementations of various embodiments are discussed in the following.

Figure 2:
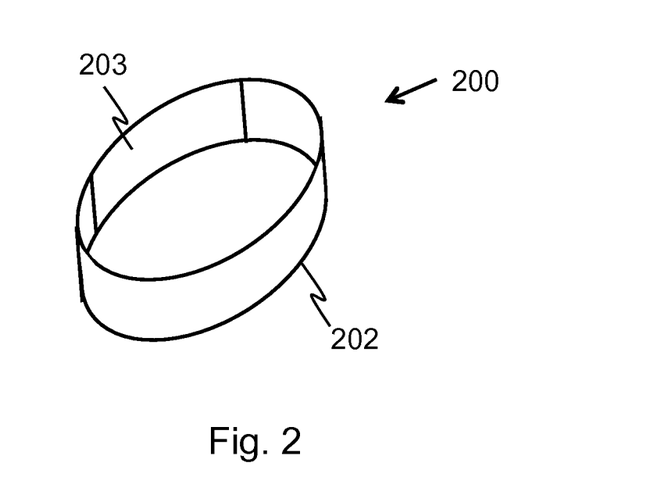
FIG. 2 is a simplified illustration of an example physiological sensor apparatus.

FIG. 2 is a simplified illustration of an example physiological sensor apparatus 200 where a sensor arrangement of various embodiments can be implemented. The apparatus 200 comprises a sensor part 203 and a strap part 202. A sensor arrangement of various embodiments may be implemented in the sensor part 203. The apparatus 200 may be a user wearable apparatus that can be fitted around a body part (e.g. wrist or ankle) of the user using the strap. The strap may be made of suitable flexible, bendable and/or stretchable material, such as plastic, fabric, and leather. In an example embodiment, the strap 202 and the sensor part 203 are integrally formed of one piece of material. The material can comprise or consist of any of the following: plastics, metals, nano-fibers, carbon fiber, leather, fabric and glass.

The sensor part 203 may be a device that is configured to be integrated into a garment of a user with or without the strap part 202. The sensor part 203 may be attached or integrated for example to a belt, a sock, a shoe, a cap, a sleeve or a collar of a shirt or pullover, and/or a waistband of trousers or skirt. The sensor part may be detachable from the garment. The sensor part 203 may be shaped like a watch and it may be configured to display time or other useful information to the user.

In an embodiment the sensor part 203 or the whole apparatus 200 may comprise flexible and rigid parts. In an embodiment the sensor part 203 or the whole apparatus 200 may comprise transparent and/or translucent sectors.

In an embodiment the sensor part 203 or the whole apparatus 200 may comprise a silicone skin adhesive layer, hydrogel, hydrocolloid and/or acrylic adhesive on the bottom side of the sensor part 203 and/or the strap 202 of the stripe to eliminate motion artefacts as well as to enable fixing the sensor part 203 freely onto any desired location in the body a user without the need to have the strap 202 at all. That is, the sensor part 203 may be attachable to the skin of the user like a plaster.

Figure 3:
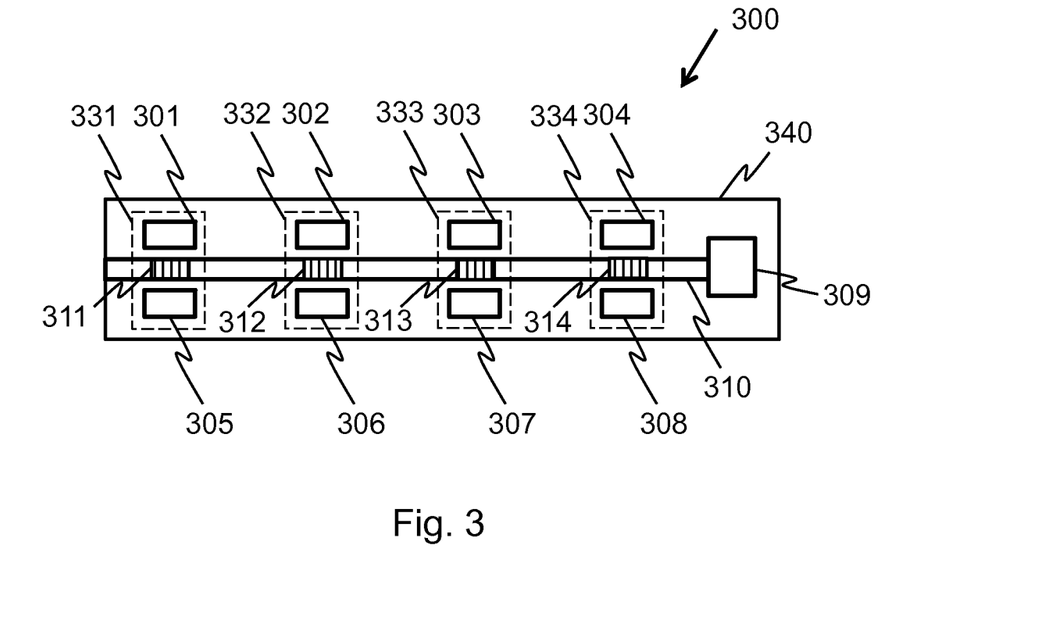
FIGS. 3-5 show bottom view illustrations of apparatuses of example embodiments.
Figure 4:
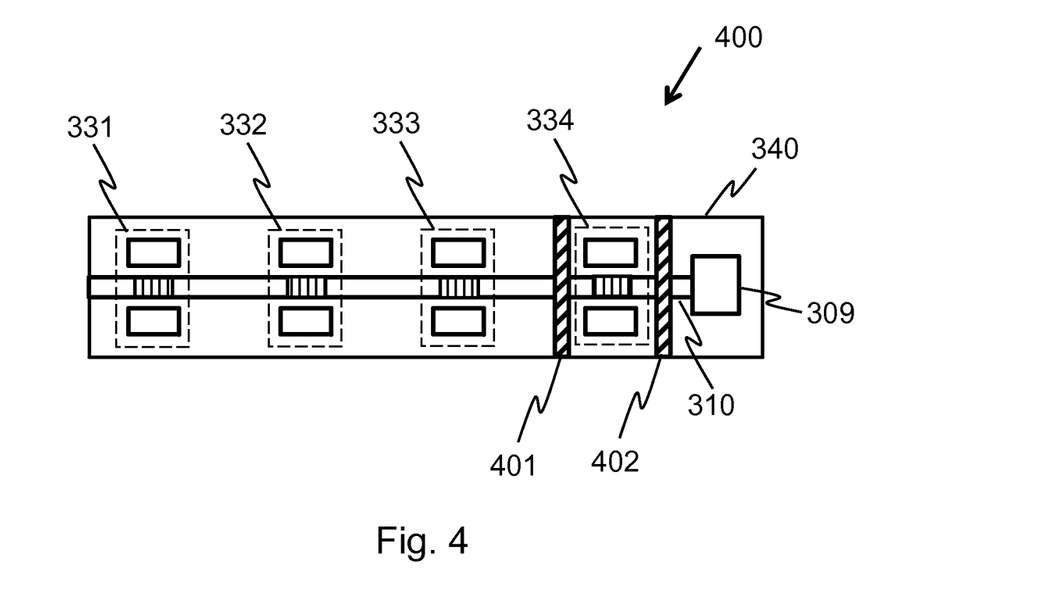
Figure 5:
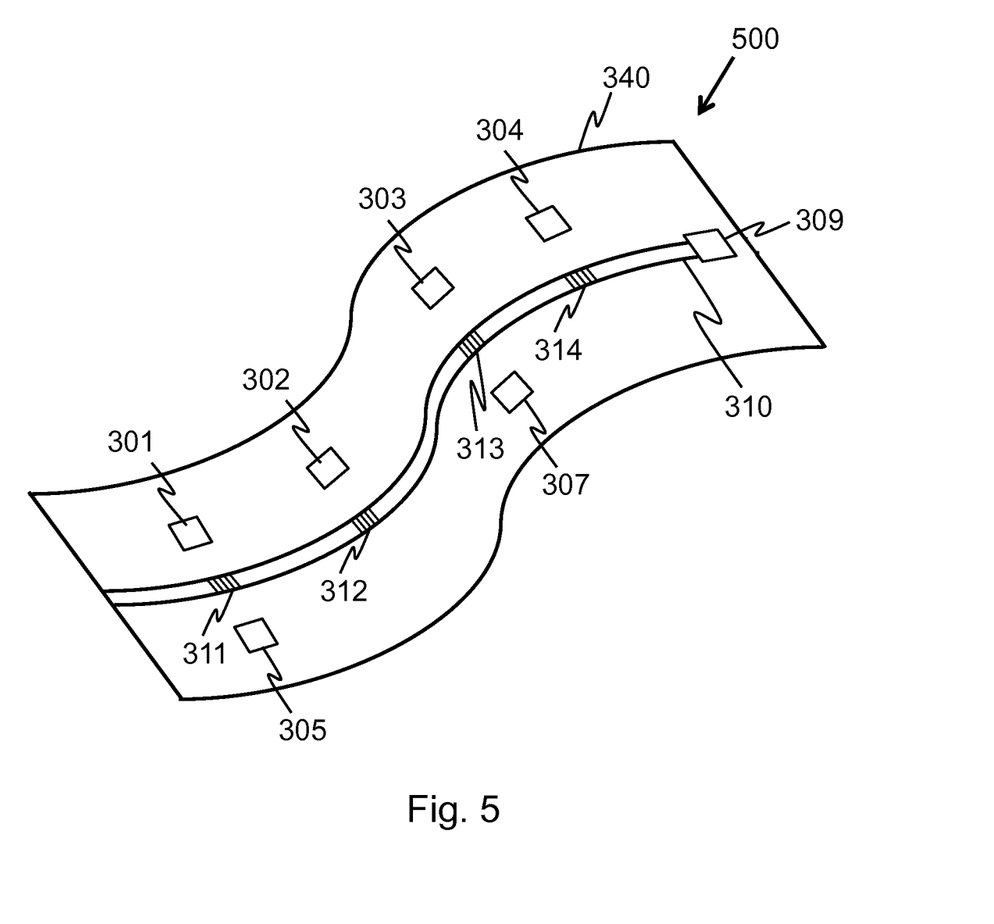

FIGS. 3-5 show bottom view illustrations of apparatuses of example embodiments.

FIG. 3 shows an apparatus 300 that comprises an elongated body part 340, a light detector 309, a plurality of light sources 301-308 and a light-conducting element 310. One end of the light-conducting element 310 is coupled to the light detector 309 so that the light-conducting element 310 guides light into the light detector 309. The light sources 301-308 are arranged into a plurality of sensing regions 331-334. In the shown example each sensing region 331-334 comprises two light sources. The light-conducting element 310 extends through the sensing regions and comprises openings 311-314 arranged at each sensing region 331-334. The openings 311-314 allow light to enter the light-conducting element 310.

The light-conducting element 310 may comprise for example a light guide, a light fibre, lenses, glass or some other optical component with suitable optical characteristics.

In an embodiment the openings 311-314 comprise a diffractive structure or a diffractive element that directs light that enters the opening into the light-conducting element 310 and through the light-conducting element 310 to the light detector 309.

The diffractive structure/element may be configured to direct light via diffraction or via refraction. The diffractive structure/element may comprise, for example, a diffractive optical element, a diffraction grating, a periodic structure/pattern and/or a series of diffraction lines/slits/grooves.

In the example of FIG. 3 each sensing region 331-334 comprises two light sources, but also other alternatives can be used. There may be for example one or three or N light sources in each sensing region. N may be for example 1, 2, 3, 5 or 10. The number of light sources does not have to be the same in each region.

The light sources 301-308 may be similar to each other or different. For example wavelengths of the light sources can be the same or different in one sensor structure. The light sources may emit for example green, red or infrared (IR) light. Also the distance between the light sources and the light-conducting element may vary between different sensing regions. In this way it is possible to vary the depth to which the light penetrates into tissue of the user.

FIG. 4 shows an apparatus 400 that represents a variation of the apparatus 300 of FIG. 3. The apparatus 400 comprises an elongated body part 340, a light detector 309, a plurality of sensing regions 331-334 and a light-conducting element 310. Similarly to the apparatus of FIG. 3 one end of the light-conducting element 310 is coupled to the light detector 309 so that the light-conducting element 310 guides light into the light detector 309. The sensing regions 331-334 comprise light sources and the light-conducting element 310 extends through the sensing regions and comprises openings arranged at each sensing region. The openings allow light to enter the light-conducting element 310.

Additionally apparatus 400 comprises electrocardiography (ECG) electrodes 401 and 402 arranged on opposite sides of the sensing region 334. The shown electrodes 401 and 402 have elongated form but it is to be understood that the shown form and placement of electrodes 401 and 402 is only one example and other arrangements are possible, too. In alternative implementations, the apparatus may comprise any number of other electrodes for the purposes of additional measurements.

FIG. 5 shows an apparatus 500 that represents a variation of the apparatuses 300 and 400 of FIGS. 3 and 4. The apparatus 500 comprises an elongated body part 340, a light detector 309, a plurality of light sources 301-305, 307 and a light-conducting element 310. One end of the light-conducting element 310 is coupled to the light detector 309 so that the light-conducting element 310 guides light into the light detector 309. The light-conducting element 310 extends from the light detector 309 along the length of the elongated body part 340 and the light-conducting element 310 comprises openings 311-314 arranged to allow light to enter the light-conducting element 310.

The light sources 301-305, 307 are arranged in vicinity of the openings 311-314 so that the light sources 301 and 305 are in vicinity of the opening 311, the light source 302 is in vicinity of the opening 312, the light sources 303 and 307 are in vicinity of the opening 313, and the light source 304 is in vicinity of the opening 314.

The elongated body part 340 is, for example, made of thin and/or flexible material. The material may be for example plastic, nano-fibre, fabric, leather or the like.

It is to be noted that any detail discussed in connection with one of apparatuses of the FIGS. 3-5 may be applied to the apparatus of one of the other FIGS. 3-5.

Figure 6A:
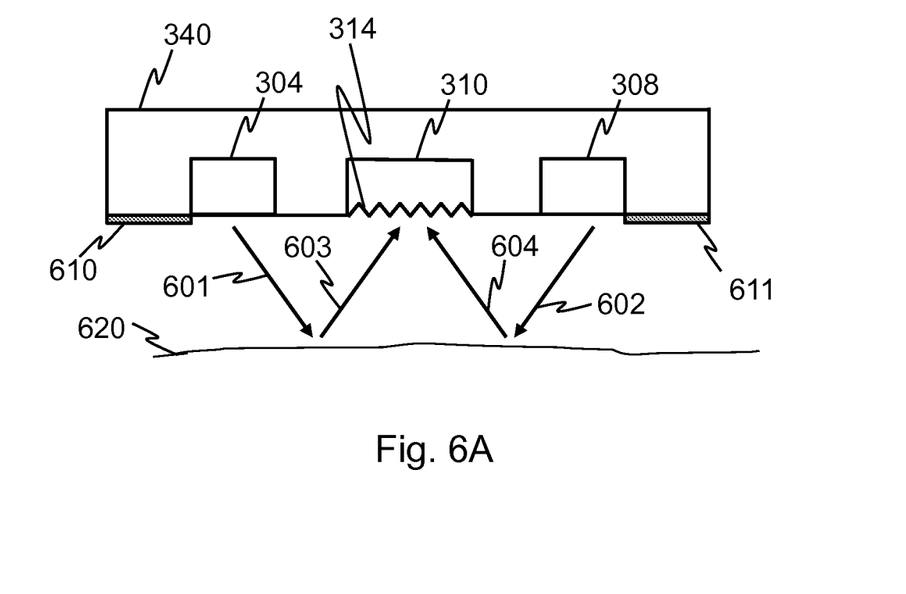
FIGS. 6A-6B show cross sectional views of the apparatus of FIG. 3.
Figure 6B:
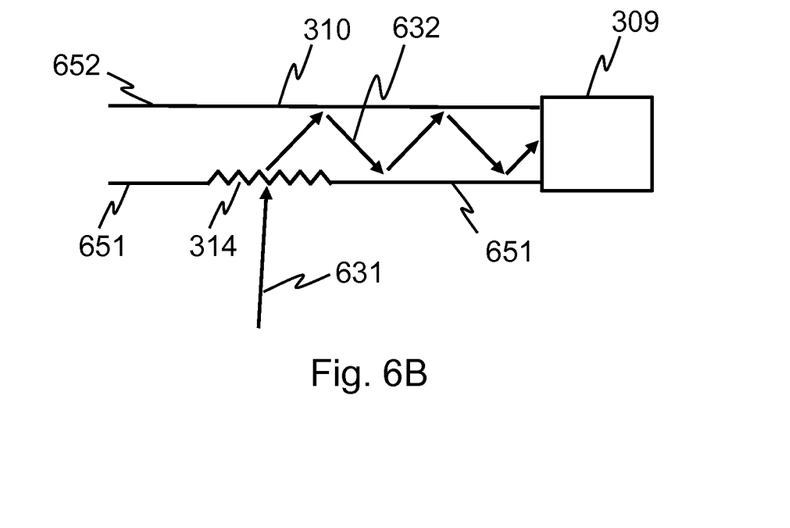

FIGS. 6A-6B show cross sectional views of the apparatus of FIG. 3 to illustrate the principle of collecting reflected light from measured skin area to one light detector.

FIG. 6A shows a cross section of the elongated body part 340, light sources 304 and 308, and light-conducting element 310. The bottom side of the light-conducting element 310 comprises diffractive structure/element 314. The bottom side of the elongated body part 340 comprises adhesive layers 610 and 611. It is noted though that this is only an example and not a mandatory feature. FIG. 6A shows also skin of a user 620.

Arrows 601 and 602 illustrate light that the light sources 304 and 308 emit. The emitted light reflects from the tissue underlying the skin of the user 620 and the reflected light illustrated by arrows 603 and 604 arrives at the diffractive structure 314 of the light-conducting element 310. The diffractive structure 314 guides the reflected light rays 603 and 604 in a controlled way into the light-conducting element 310 and therethrough to the light detector (not shown in FIG. 6A).

One needs to note that for illustrative purposes FIG. 6A shows a gap between the sensor and the skin, but that in an actual implementation there is likely no such gap. Instead the sensor 340 touches the skin 620 or the gap is relatively small.

FIG. 6B shows a cross section of the light-conducting element 310 and the light detector 309. The bottom side of the light-conducting element 310 comprises diffractive structure/element 314. A light ray 631 that arrives at the diffractive structure 314 is guided by the diffractive structure 314 into the light-conducting element 310. Inside the light-conducting element 310 (such as a light guide) the light reflects and travel based on Schnell laws as illustrated by arrows 632 and thereby the light ray is conducted to the light detector 309.

In an embodiment, the light-conducting element 310 comprises coating configured to prevent light rays from leaking out of the light-conducting element. The coating may be located e.g. on the surface 651 of the light-conducting element or on the surface 652 of the light-conducting element or on both of these. The coating may be for example mirror or some other suitable coating.

In an embodiment, there exist more than one co-located light detectors, while the light-conducting element conveys reflected light to all of these co-located light detectors.

There may be for example two or more parallel light detectors. The co-located light detectors may be sensitive to different wavelengths.

Figure 7A:
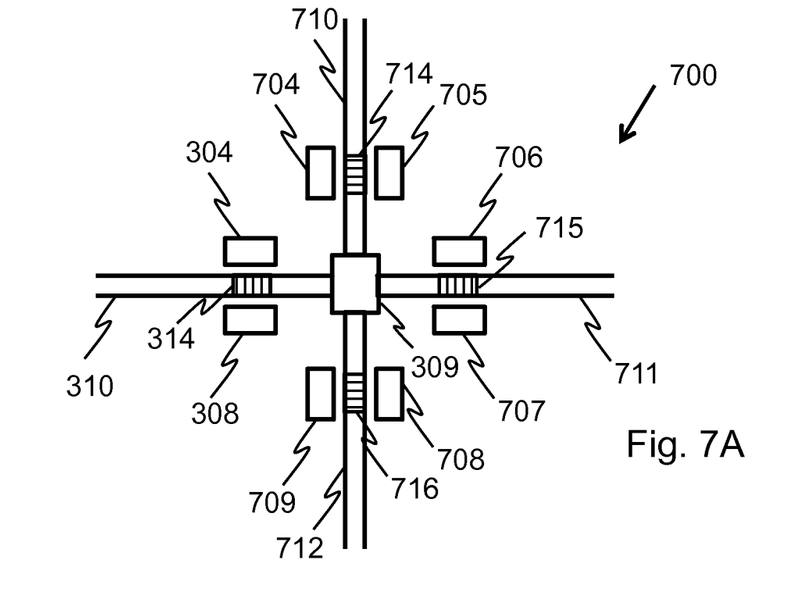
FIGS. 7A-7C illustrate some further implementation examples.
Figure 7B:
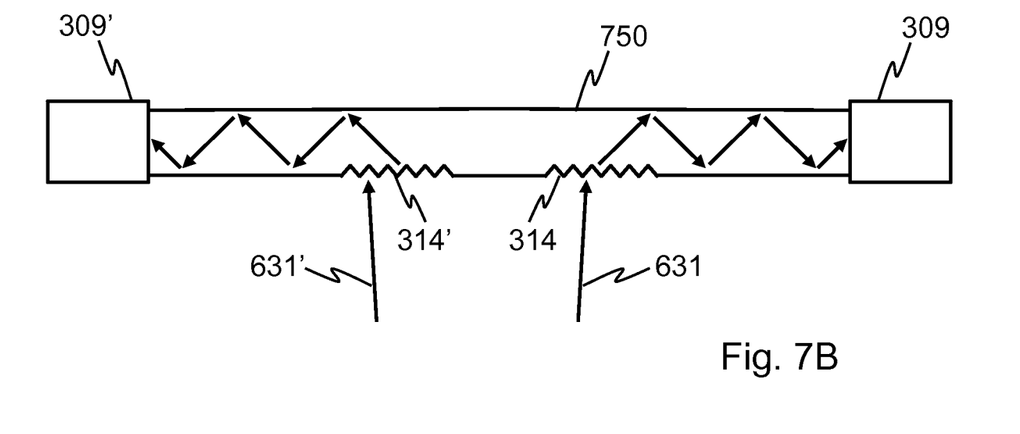
Figure 7C:
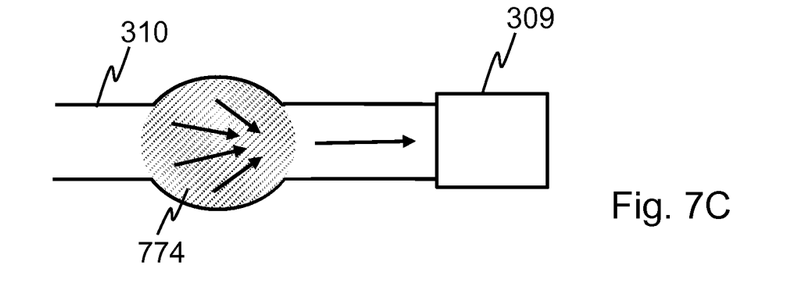

FIGS. 7A-7C illustrate some further implementation examples. All of these may be combined with each other or with example implementations discussed in the foregoing.

FIG. 7A is a bottom view illustration of an example with more than one light guide/collecting light from more than one direction. The apparatus 700 of FIG. 7A comprises a light detector 309 and light-conducting elements 310, 710, 711 and 712 coupled to the light detector 309 so that the light-conducting elements 310, 710, 711 and 712 guide light into the light detector 309. The light-conducting elements 310, 710-712 comprise diffractive structures/elements 314, 714-716 that allow light rays to enter the light-conducting elements. Further, the apparatus 700 comprises a plurality of light sources 304, 308, 704-709 in vicinity of the diffractive structures/elements 314, 714-716. Only one diffractive element is shown on each light-conducting element, but there may be more than one diffractive elements.

FIG. 7B is a cross-sectional illustration of an example where light is guided to different directions in the light-conducting element. The shown apparatus comprises light detectors 309 and 309' and a light-conducting element 750. One end of the light-conducting element 750 is coupled to the light detector 309 and the other end of the light-conducting element is coupled to the light detector 309'. There are diffractive elements 314 and 314' on the side of the light-conducting element 750. The diffractive elements 314 and 314' are configured to guide light to different directions towards different light detectors so that light rays 631 that enter the diffractive element 314 are guided to the light detector 309 and light rays 631' that enter the diffractive element 314' are guided to the light detector 309'.

FIG. 7C is a bottom view illustration of an example where reflected light form a larger area is collected. The shown apparatus comprises a light detector and a light-conducting element 310. One end of the light-conducting element 310 is coupled to the light detector 309. Further the apparatus comprises a diffractive structure/element 774 configured to guide light into the light-conducting element 310. In the shown example the area covered by the diffractive element is larger than the cross section of the light-conducting element 310 whereby light from a larger area is collected.

Yet another implementation example is to include two light detectors and two light-conducting elements e.g. in the apparatus of FIG. 3. The light-conducting elements may be parallel or interlaced or intertwined. In such implementation the openings into the light-conducting elements may be placed so that if some sensing region of one of the light-conducting elements is adversely affected by ambient light at least the other light-conducting element is likely to produce better measurement signals. It is understood that various different geometries are possible.

In implementations including more than one light-conducting element, the elements may be built into the same material or the elements may be separate components. Additionally or alternatively, the light-conducting element may comprise multiple material layers for different wavelengths.

Figure 8:
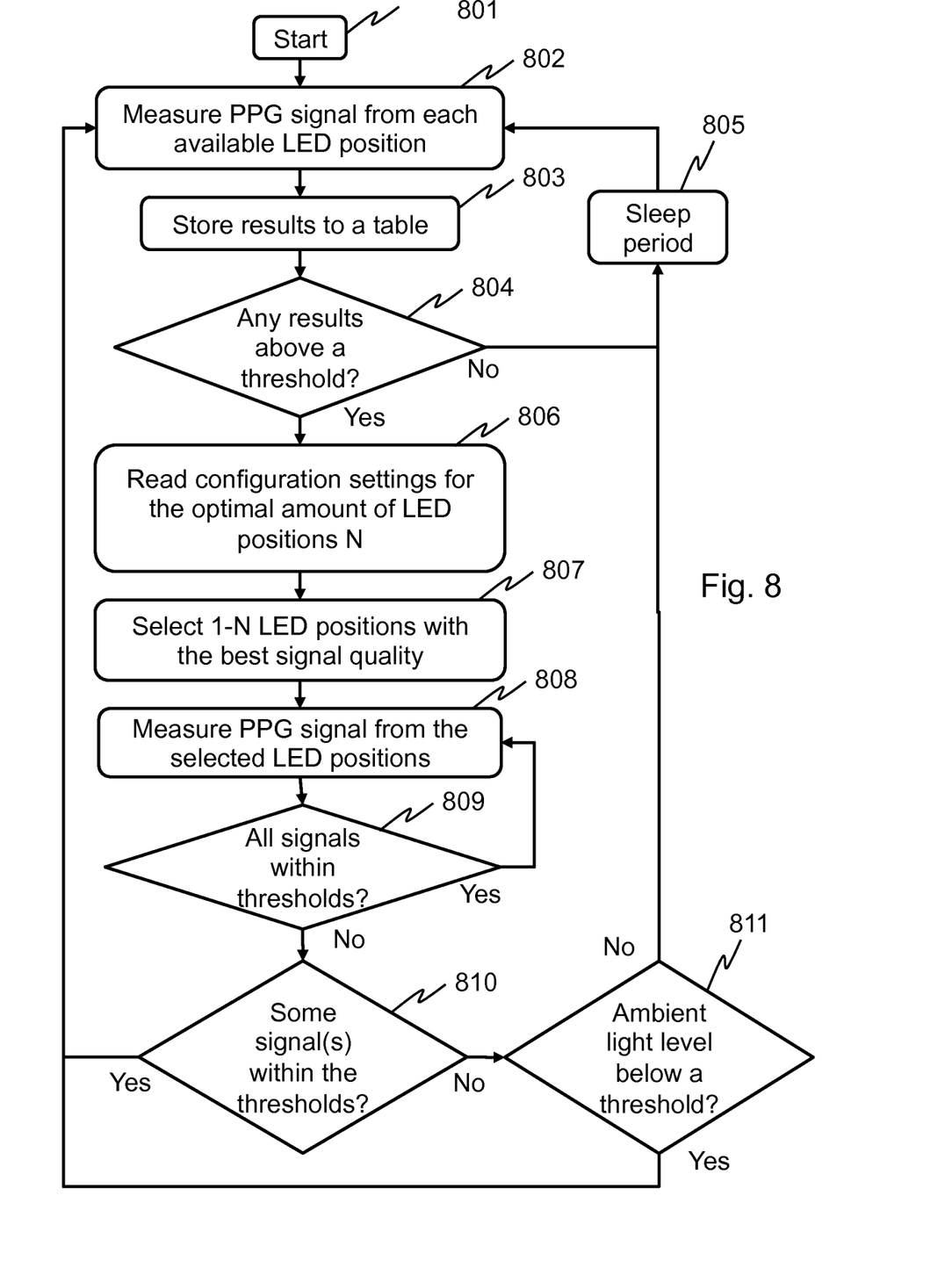
FIG. 8 shows a flow chart of a process of an example embodiment.

FIG. 8 shows a flow chart of a process of an example embodiment. The process may be implemented for example in one of the apparatuses of FIGS. 3-7C in a processor or other processing element that controls operation of the light sources and the light detector(s). The processor is not shown in FIGS. 3-7C, but it is clear that such processor can be implemented in a user wearable apparatus.

The process of this example embodiment concerns PPG measurement, but the process can be adapted for other optical measurements, too. The process comprises the following phases:

801: The process is started.

802: PPG signal is measured from each available LED position or sensing region. In an example implementation the LEDs in each position or sensing region are turned on and off consecutively to separately measure each position and to obtain plurality of measurement results. In an alternative embodiment the openings into the light-conducting element in each sensing region are opened and closed consecutively to separately measure each position and to obtain plurality of measurement results. For example LCD or electrowetting can be used for opening and closing the openings. Also mechanical opening and closing of the openings is possible. It is to be noted that in this example all available measurement positions are measured, but in alternative embodiments only some subset of the positions are measured. That is, it is not mandatory to always measure all available positions.

803: The measurement results are stored in a table for further processing.

804: It is checked, if any of the measurement results exceed a previously set threshold value. If none of the results exceeds the threshold, the process moves to sleep period in phase 805 (as reasonable measurement results cannot be obtained). From the sleep period of the phase 805, the process returns to the phase 802 to measure each LED position. It is noted that in this example, certain thresholds are used. Alternatively or additionally, some other signal quality criteria may be used, too.

806: If results that exceed the threshold exist, the process moves to phase 806 to read configuration settings to find out optimal or desired amount of LED positions N. N may be any number between 1 and maximum number of LEDs included in the arrangement. N may be for example 1, 2, 3, 5 or 10.

807: 1-N LED positions are selected for the measurement. For example the positions with the best signal quality may be selected or any positions that exceed the threshold may be selected.

808: PPG signal is measured from the selected LED positions or sensing regions. Different positions may be measured consecutively, for example.

809: It is checked, if the measurement results from the selected LED positions are within previously set thresholds. If yes, the process continues to measure the selected LED positions in phase 808.

810: If all measurement results from the selected LED positions are not within the previously set thresholds, it is checked if at least some of them are. If yes, the process returns to phase 802 to measure all LED positions.

811: If none of the measurement results are within the thresholds, it is checked if ambient light level at some of the available LED positions is below a previously set threshold. If yes, the process returns to phase 802 to measure all LED positions. If the ambient light level is not below the threshold, the process moves to sleep period in phase 805 (as reasonable measurement results cannot be obtained).

In addition to the phases shown in FIG. 8, the process may comprise checking if there is sufficient battery level to continue measurements, and if not, the process ends.

In an example embodiment, the signal levels from different sensing regions or different light sources are calibrated prior to performing actual measurement or even during the measurement. The calibration phase allows taking into account that the distance between the light sources and the respective diffractive element and/or the distance the light travels in the light-conducting element and/or possible leakage of light from the other diffractive elements may attenuate the detected light in different ways.

It is noted that for example the use of more than one light-conducting element allows reducing possible leakage of light through the other diffractive elements along the length of the light-conducting element. Also embodiments where the openings into the light-conducting element are opened and closed allow reducing possible leakage of light through the other diffractive elements/openings along the length of the light-conducting element.

It is to be noted that FIG. 8 illustrates an example implementation and that variations of changes to the shown process are possible. For example some of the shown phases are not necessarily needed and the order of the phases may be changed to some extent. For example, it may be fixed how many LED positions are measured, whereby phase 806 is not needed. Additionally or alternatively, for example checking the ambient light level is not mandatory.

Without in any way limiting the scope, interpretation, or application of the claims appearing below, a technical effect of one or more of the example embodiments disclosed herein is improved physiological measurement.

Another technical effect of one or more of the example embodiments disclosed herein is ability to construct a thin sensor strip with plurality of sensing regions. Yet another technical effect of one or more of the example embodiments disclosed herein is that one detector component may suffice for measurement form a plurality of spatially separate locations.

Another technical effect of one or more of the example embodiments disclosed herein is more flexibility in sensor designing. Individual physiological differences between users may cause challenges when one tries to position a single physiological measurement sensor optimally for the measurement. For example the exact location of blood vessels varies between individuals, movements of the user may move the sensor to a non-optimum location during measurement, and repositioning the sensor may be difficult. In example embodiments, it is not that important to be able to position one exact region of the sensor at certain location on a user's body as multiple locations can be measured. In this way one achieves that the effects of the individual physiological differences between users to the measurement are reduced.

Another technical effect of one or more of the example embodiments disclosed herein is that single sensor can be used for effecting measurement at multiple locations, that is, flexible selection of measurement points is provided. Thereby sensor positioning is not that crucial anymore as the sensor is able to adapt to changing conditions and individual physiological differences. Another technical effect of one or more of the example embodiments disclosed herein is that extensive amount of additional components are not needed for effecting the measurement at multiple locations. The embodiments enable for example use of one light detector with multiple light sources.

Another technical effect of one or more of the example embodiments disclosed herein is ability to produce sensors in soft, flexible strip or band that is easy to wear. Another technical effect of one or more of the example embodiments disclosed herein is that the same implementation can be used for measurements on different parts of human body, e.g. around wrist, arm, leg, on or around chest, on forehead etc.

If desired, the different functions discussed herein may be performed in a different order and/or concurrently with each other. Furthermore, if desired, one or more of the before-described functions may be optional or may be combined.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the foregoing describes example embodiments of the invention, these descriptions should not be viewed in a limiting sense. Rather, there are several variations and modifications which may be made without departing from the scope of the present invention as defined in the appended claims.

The invention claimed is:

1. An apparatus comprising:
   a plurality of light sources configured to emit light for reflection from tissue of a user wearing the apparatus,
   at least one light detector configured to detect light that enters the light detector to produce a detected signal for a physiological measurement, and
   a light-conducting element configured to conduct light to the light detector, wherein the light-conducting element is configured to allow light reflected from the tissue of the user to enter the light-conducting element at a plurality of spatially separated locations along a length of the light-conducting element, where the light-conducting element is configured and located relative to the plurality of light sources to allow the reflected light to enter the light-conducting element without the light from the plurality of light sources directly entering the light-conducting element,
   wherein the apparatus comprises openings at said plurality of locations, the openings allowing light to enter the light-conducting element, wherein said plurality of light sources are arranged into a plurality of sensing regions, each sensing region comprising at least one of the light sources, and wherein the light-conducting element extends through the sensing regions, each sensing region comprising at least one of said openings in a vicinity of the respective at least one light source.

2. The apparatus of claim 1, wherein the light-conducting element is a longitudinal element, with one end of the light conducting-element being coupled to the light detector and the other end longitudinally extending away from the light detector, and wherein the plurality of light sources and the openings are located along the length of the light-conducting element.

3. The apparatus of claim 1, wherein the light-conducting element is a light guide.

4. The apparatus of claim 1, wherein the apparatus comprises diffractive structures at said plurality of locations to guide the light reflected from the tissue of the user into the light-conducting element.

5. The apparatus of claim 4, wherein the diffractive structures comprise one or more of the following:
   a diffractive optical member,
   a diffraction grating,
   a periodic diffractive pattern, or
   a series of diffraction lines.

6. The apparatus of claim 1, wherein the apparatus comprises a plurality of said light detectors.

7. The apparatus of claim 1, wherein the apparatus comprises a plurality of said light-conducting elements.

8. The apparatus of claim 1, wherein the apparatus comprises two or more pairs of said light detectors and light-conducting elements.

9. A user wearable apparatus comprising a frame and the apparatus of claim 1 connected to the frame.

10. The apparatus as claimed in claim 1 further comprising a processor configured to:
    obtain a plurality of detected signals using the detector and different ones of the light sources, and
    select, based on the obtained plurality of detected signals, one or more of the plurality of light sources for use in the physiological measurement,
    where the selected one or more light sources provide a signal that meets a predefined quality criterion.

11. The apparatus as claimed in claim 1 where exits from the plurality of light sources, of the light emitted by the plurality of light sources, are located at a same side of the apparatus as entrances to the light-conducting element at the spatially separated locations.

12. The apparatus as claimed in claim 11 where the entrances to the light-conducting element at the spatially separated locations each comprise a diffractive structure configured to direct at least some of the reflective light entering the light-conducting element at the spatially separated locations towards the at least one light detector.

13. The apparatus as claimed in claim 11 further comprising a frame, where the exits of the plurality of light sources are located at a same side of the frame as entrances to the light-conducting element at the spatially separated locations.

14. The apparatus as claimed in claim 13 where the exits of the plurality of light sources are spaced at the same side of the frame from the entrances to the light-conducting element.

15. A method for using a sensor arrangement of a user wearable apparatus, the sensor arrangement comprising a plurality of light sources configured to emit light for reflection from tissue of a user wearing the user wearable apparatus, at least one light detector configured to detect light that enters the light detector to produce a detected signal for a physiological measurement, and a light-conducting element configured to conduct light to the light detector, wherein the light-conducting element is configured to allow light reflected from the tissue of the user to enter the light-conducting element at a plurality of spatially separated locations along a length of the light-conducting element, where the light-conducting element is configured and located relative to the plurality of light sources to allow the reflected light to enter the light-conducting element without the light from the plurality of light sources directly entering the light-conducting element, wherein the method comprises:

obtaining a plurality of measurement signals using different ones of the plurality of light sources, and based on the obtained measurement signals, selecting at least two of the plurality of light sources for use in the physiological measurement.

16. The method of claim 15, further comprising selectively turning on and off the plurality of light sources to obtain the plurality of measurement signals.

17. The method of claim 15, further comprising selectively opening and closing the spatially separate locations to obtain the plurality of measurement signals.

18. The method of claim 15, where the selecting of the one or more light sources for use in the physiological measurement comprises selecting the one or more light sources that provide a signal that meets a pre-defined quality criterion, and the method further comprises:

limiting use of the plurality of light sources to use of the selected one or more light sources that meets the pre-defined quality criterion for the physiological measurement.

* * * * *